US006633776B2

(12) United States Patent
Levine et al.

(10) Patent No.: US 6,633,776 B2
(45) Date of Patent: Oct. 14, 2003

(54) METHOD AND APPARATUS FOR GENERATING AND DISPLAYING LOCATION-SPECIFIC DIAGNOSTIC INFORMATION USING AN IMPLANTABLE CARDIAC STIMULATION DEVICE AND AN EXTERNAL PROGRAMMER

(75) Inventors: Paul A. Levine, Santa Clarita, CA (US); Gregory C. Bevan, Canyon Country, CA (US)

(73) Assignee: Pacesetter, Inc., Sylmar, CA (US)

( * ) Notice: Subject to any disclaimer, the term of this patent is extended or adjusted under 35 U.S.C. 154(b) by 188 days.

(21) Appl. No.: 09/822,887

(22) Filed: Mar. 30, 2001

(65) Prior Publication Data

US 2003/0088289 A1 May 8, 2003

(51) Int. Cl.$^7$ .............................................. A61B 5/044
(52) U.S. Cl. .......................... 600/523; 607/30; 607/59
(58) Field of Search ........................... 607/2–9, 32, 30, 607/59; 600/522–523, 510, 524, 525, 374

(56) References Cited

U.S. PATENT DOCUMENTS

| | | | | |
|---|---|---|---|---|
| 4,809,697 A | | 3/1989 | Causey, III et al. | 128/419 |
| 4,944,299 A | | 7/1990 | Silvian | 128/419 |
| 5,431,691 A | * | 7/1995 | Snell et al. | 607/27 |
| 5,466,254 A | | 11/1995 | Helland | 607/123 |
| 5,716,382 A | | 2/1998 | Snell | 607/30 |
| 5,948,005 A | * | 9/1999 | Valikai et al. | 607/32 |
| 5,974,341 A | * | 10/1999 | Er et al. | 607/31 |

\* cited by examiner

Primary Examiner—Angela D. Sykes
Assistant Examiner—Jeanne Yu

(57) ABSTRACT

Location-specific diagnostic information is detected and recorded by the cardiac stimulation device for subsequent display using the external programmer device. The diagnostic information includes location-specific event records, counters and IEGM signals. The event records include event codes that distinguish among events occurring in the four chambers of the heart, such as sensed or paced events occurring within the left or right atria or the left or right ventricles. The counters separately count events occurring within the chambers of the heart. The IEGM signals are separately detected within the four chambers of the heart using a multiple sensing lead arrangement. The location-specific event records, counters and IEGM signals are ultimately transmitted to the external programmer, which displays graphic representations of the diagnostic information. The event records are displayed using distinct event marker icons which distinguish among the four chambers of the heart. The distinct event marker icons are displayed along with location-specific IEGM displays or surface ECG displays to permit a physician operating the programmer to easily identify the specific chambers of the heart in which events the occurred. Additionally, the programmer displays the values of the various counters to provide, for example, a set of location-specific histograms. The diagnostic information detected and recorded by the stimulation device and displayed by the external programmer device may further distinguish among events detected at multiple locations within each chamber of the heart. Method and apparatus embodiments are described.

39 Claims, 7 Drawing Sheets

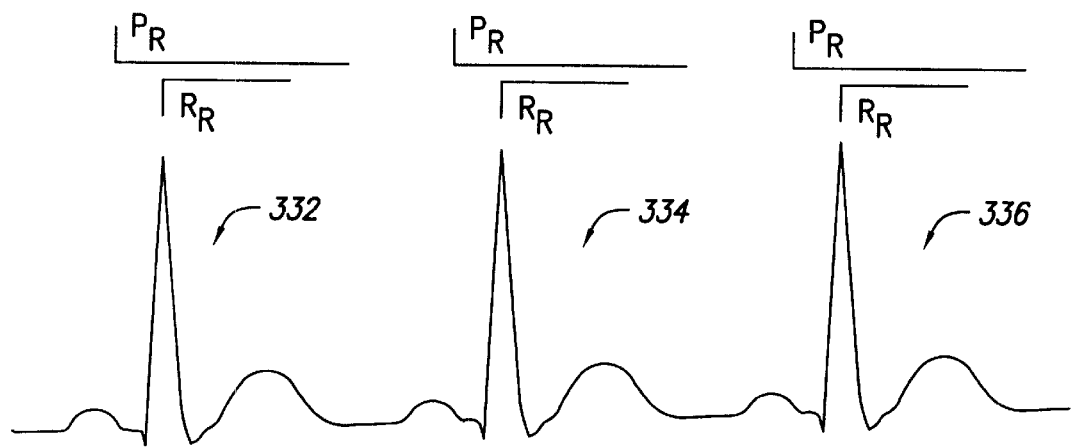
FIG. 8
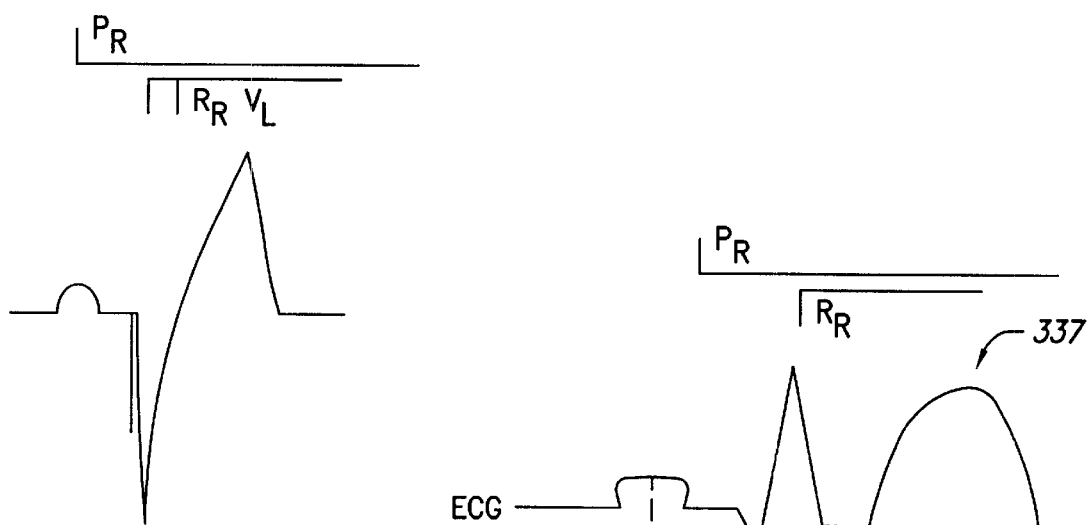
FIG. 9
FIG. 10

METHOD AND APPARATUS FOR GENERATING AND DISPLAYING LOCATION-SPECIFIC DIAGNOSTIC INFORMATION USING AN IMPLANTABLE CARDIAC STIMULATION DEVICE AND AN EXTERNAL PROGRAMMER

FIELD OF THE INVENTION

The invention generally relates to implantable cardiac stimulation devices and to external programmers used in connection therewith and in particular to methods and apparatus for processing and displaying event markers and other diagnostic information detected by an implanted device.

BACKGROUND OF THE INVENTION

A wide variety of implantable cardiac stimulation devices are provided for surgical implantation into patients. One common example is the cardiac pacemaker. Another is the internal cardioverter defibrillator (ICD). Implantable devices are often configured to be used in conjunction with an external programmer that allows a physician to display information detected by the implanted device. For example, the external programmer may operate to display electrical cardiac signals detected by the implantable device in the form of intracardiac electrograms (IEGMs). An IEGM is a graphic depiction of electrical signals emitted by active cardiac tissue as detected by electrodes placed in the heart. The electrical signals are digitized and recorded with the implanted device along with an indication of the date and time, then transmitted to the external programmer for display thereon, perhaps during a subsequent follow-up session with the physician. Alternatively, the implanted device is controlled to transmit the IEGM signals in real-time during the follow-up session. The external programmer may also be configured to receive real-time surface electrocardiogram (ECG) signals from an external ECG detector, perhaps for display along with contemporaneous real-time IEGM signals transmitted from the implanted device.

The implanted device may also be configured to detect various events, such as paced and sensed events, and to generate event codes representative of the events for transmission to the external programmer. The event codes are detected and stored in the implanted device along with the corresponding IEGM signals and the date and time for subsequent transmission to the external programmer or are detected and transmitted to the external programmer in real-time along with real-time IEGM signals. The external programmer generates event marker icons based on the code and displays the icons along with either IEGM signals, ECG signals, or both. Exemplary event markers are: P for a sensed event in the atria; R for a sensed event in the ventricles; A for a paced event in the atria, and V for a paced event in the ventricles. Along with the event markers, the programmer may also display variable length horizontal lines representative of the length of atrial and ventricular refractory periods associated with the events along with numerical values indicative of measured intervals between atrial and ventricular events, based on still further information recorded and transmitted by the implantable device. The external programmer may also display additional information received from the implanted device such as numerical information identifying the heart rate and the duration of ventricular and atrial refractory periods. Also, the display may provide other event markers as well, such as event markers indicating mode switching events. The implanted device may also maintain counters for counting various events, such as paced and sensed atrial and ventricular event counters, for subsequent transmission to and display using the external programmer.

An exemplary surface ECG display, along with event markers, is provided in FIG. 1. More specifically, FIG. 1 illustrates three ECG complexes (denoted 2, 4 and 6), along with P and R event markers indicating that the atrial and ventricular events are both intrinsic events. For both the P and R events, the display also includes horizontal lines adjacent thereto that indicate the length of the corresponding refractory period. Although not shown in FIG. 1, the external programmer may display additional information received from the implanted device such as IEGM signals.

Such displays of event markers and counters are helpful in permitting the physician to analyze the operation of the implanted device and to diagnose arrhythmias, if any, within the patient. U.S. Pat. No. 5,431,691 to Snell et al. entitled "Method and System for Recording and Displaying a Sequential Series of Pacing Events" provides a description of the operation of an exemplary pacemaker and external programmer including a detailed description of the generation, transmission and display of IEGM data and event markers. U.S. Pat. No. 5,431,691 to Snell et al. is incorporated by reference herein.

Although the typical event codes and counters maintained by implantable devices and the typical event marker icons displayed by external programmers are quite helpful to the physician, room for improvement remains. In particular, state of the art implantable devices are being developed utilizing multiple sensing/pacing leads for pacing or sensing at multiple locations within the heart. For example, separate leads may be provided to the left and right atria, as well as to left and right ventricles. In other cases, a single atrial lead may be capable of sensing and pacing in both the left and right atria, and a single ventricular lead may be capable of sensing and pacing in the left and right ventricles. Devices are also being developed which permit sensing or pacing at two or more locations within a single chamber. Eventually, highly sophisticated devices may be developed which permit sensing and pacing at a large number of locations within each chamber of the heart. As can be appreciated, when using such systems, the aforementioned conventional event codes, counters and event marker icons, which typically distinguish only between the atria and the ventricles may not be sufficient. Consider again the display of FIG. 1. The intrinsic events of the ECG complexes 2 and 6 may have been detected only within the right atrium and ventricle whereas the intrinsic events of the ECG complex 4 may have been detected only within the left atrium and ventricle. Yet, the events markers indicate no such distinction been the left and right chamber events. Moreover, because the complexes themselves are derived from a surface ECG, rather than an IEGM, the complexes contain no polarization information that might permit the physician to distinguish between the left and right chamber events.

Accordingly, there is a need to develop enhanced event codes, event marker icons and event counters which accommodate implantable devices capable of separately sensing and pacing in the left or right chambers of the heart, or at multiple locations within a single chamber of the heart. There is also a need to develop improved hardware and software for use within implantable devices and within external programmers for recording, tracking and displaying the enhanced codes and markers. It is to these ends that aspects of the invention are primarily directed.

SUMMARY OF THE INVENTION

In accordance with a first aspect of the invention, a system is provided for use in an implantable cardiac stimulation device for generating diagnostic information using enhanced event codes. The enhanced event codes are representative of events detected using a plurality of leads positioned at different locations within the heart, with at least two leads positioned within the atria or with at least two leads positioned within the ventricles. The system includes means for receiving signals representative of electrical events detected at the respective locations of the leads, means for generating stimulation signals using selected leads, and means for generating location-specific event codes representative of events occurring at the respective locations of the leads. The location-specific event codes correspond to the arrangement of leads and hence include at least two distinct event codes associated the atria or at least two distinct event codes associated with the ventricles. The system also includes means for transmitting the location-specific event codes to an external programmer for display thereon.

In accordance with a second aspect of the invention, an external programmer is provided for use with an implantable cardiac stimulation device for displaying diagnostic information received from the stimulation device using enhanced event marker icons. The external programmer includes means for receiving location-specific event codes transmitted from the stimulation device and means for generating graphic displays of location-specific event marker icons representative of the event codes, with a distinct location-specific event marker icon associated with each distinct location-specific event code. The location-specific event codes provided by the stimulation device correspond to the arrangement of leads of the stimulation device, which includes at least two leads in the atria or at least two leads in the ventricles.

By employing the enhanced location-specific event codes and event marker icons, the diagnostic information provided by the stimulation device and displayed by the external programmer thereby distinguishes events sensed in the left atrium from events sensed in the right atrium and distinguishes events sensed in the left ventricle from events sensed in the right ventricle. If separate sensing locations are provided within each of the four chambers of the heart, the diagnostic information distinguishes electrical events occurring in any particular chamber of the heart from all other chambers of the heart. If multiple sensing locations are provided within a particular chamber of the heart, the diagnostic information distinguishes among electrical events occurring at each of the various locations within the chamber. Location-specific event counters may be provided for separately counting events occurring at the respective locations of the leads so as to permit, for example, display of location-specific event histograms. The stimulation device and external programmer thereby provide more effective tracking of electrical events within the heart and permit more sophisticated displays of diagnostic information.

In one specific example, wherein the stimulation device has pacing/sensing leads within each of the four chambers of the heart, the external programmer displays $P_R$ and $P_L$ event marker icons representative of sensed events in the right and left atria, respectively, and $R_R$ and $R_L$ event marker icons representative of sensed events in the right and left ventricles, respectively. If the stimulation device is capable of pacing in either the left ventricle, the right ventricle, or both ventricles simultaneously, the external programmer displays $V_L$, $V_R$, and $V_D$ event marker icons, respectively. If the stimulation device is also capable of pacing in the left and right atria, the external programmer additionally displays $A_L$, $A_R$ and $A_D$ event marker icons, respectively. For stimulation devices capable of pacing or sensing at multiple locations within a single chamber, additional subscripted indices are employed indicating the specific location within the chamber. A vertical tick mark is displayed by the external programmer adjacent the each event marker icon to indicate the exact time of the corresponding event. If an intrinsic event sensed in one chamber triggers a stimulation event in another chamber, the external programmer displays two vertical tick marks adjacent to one another along with a pair of event marker icons identifying the sensed and triggered events. Horizontal lines are displayed to indicate the duration of corresponding refractory periods. The event marker icons are displayed adjacent surface ECG signals or IEGM signals, or both. Separate location-specific IEGM signals may be displayed, including, for example, a separate IEGM signal per chamber. The external programmer may also be programmed to display location-specific histograms, such as one histogram for right atrial intrinsic events as a function of heart rate and another histogram of left atrial intrinsic events as a function of heart rate.

Other objects and advantages of the invention are achieved as well. Method embodiments of the invention are also provided.

BRIEF DESCRIPTION OF THE DRAWINGS

Further features and advantages of the invention may be more readily understood by reference to the following description taken in conjunction with the accompanying drawings, in which:

FIG. 6 is a block diagram illustrating a portion of a memory of the external programmer of FIG. 5 for the storing enhanced location-specific event codes, counters and IEGM signals received from the stimulation device;

FIG. 8 is a graph illustrating exemplary ECG complexes along with enhanced event markers that distinguish among the four chambers of the heart as displayed by the external programmer of FIG. 5;

FIG. 9 is a graph illustrating another exemplary ECG complex as displayed by the external programmer of FIG. 5;

FIG. 10 is a graph illustrating another exemplary ECG complex along with atrial and ventricular IEGM signals as displayed by the external programmer of FIG. 5.

DETAILED DESCRIPTION OF THE INVENTION

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

The description is of a system having an implantable cardiac stimulation device for implantation into a patient and an external programmer for programming the operation of the implantable device and for processing and displaying diagnostic information received from the implantable device regarding the condition of the patient and regarding the condition of the implantable device itself. The diagnostic information displayed by the external programmer includes enhanced location-specific event marker icons.

Figure 2:
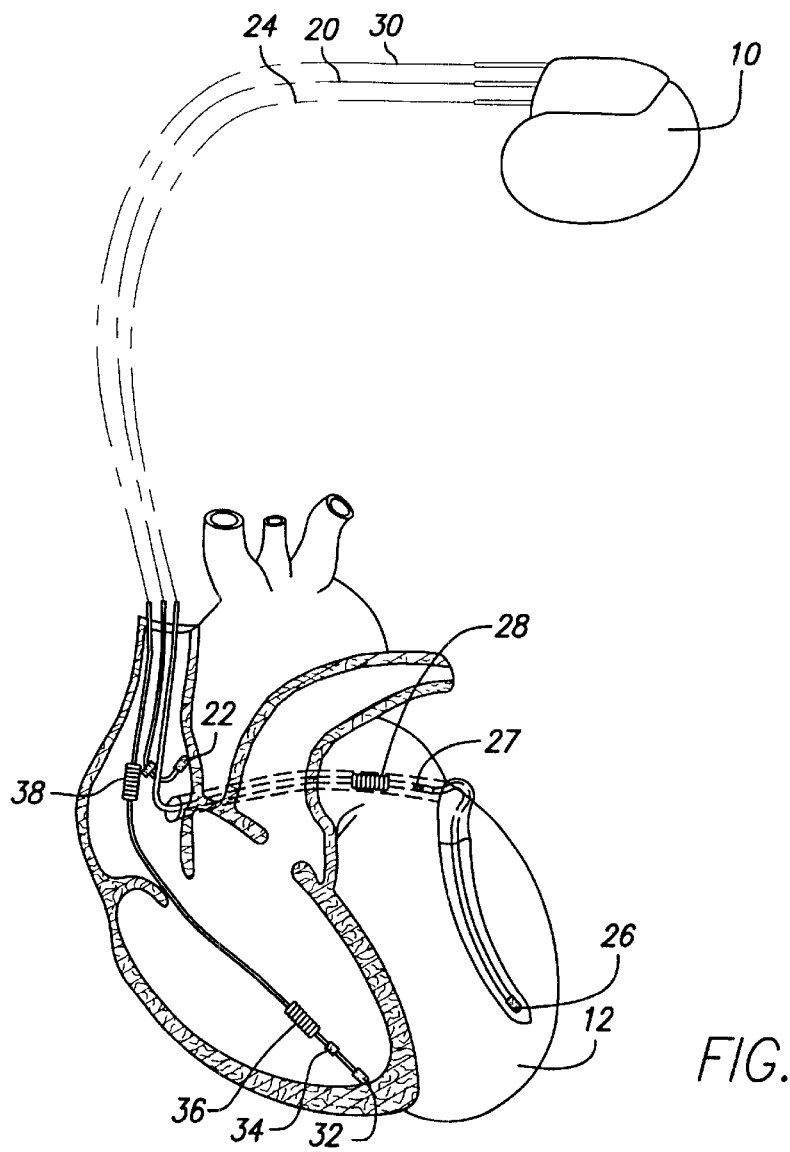
FIG. 2 is a simplified diagram illustrating an implantable stimulation device in electrical communication with at least three sensing leads implanted into a patient's heart for delivering multi-chamber stimulation and shock therapy and for sensing intrinsic heart signals within each of the four chambers of the heart.
Figure 3:
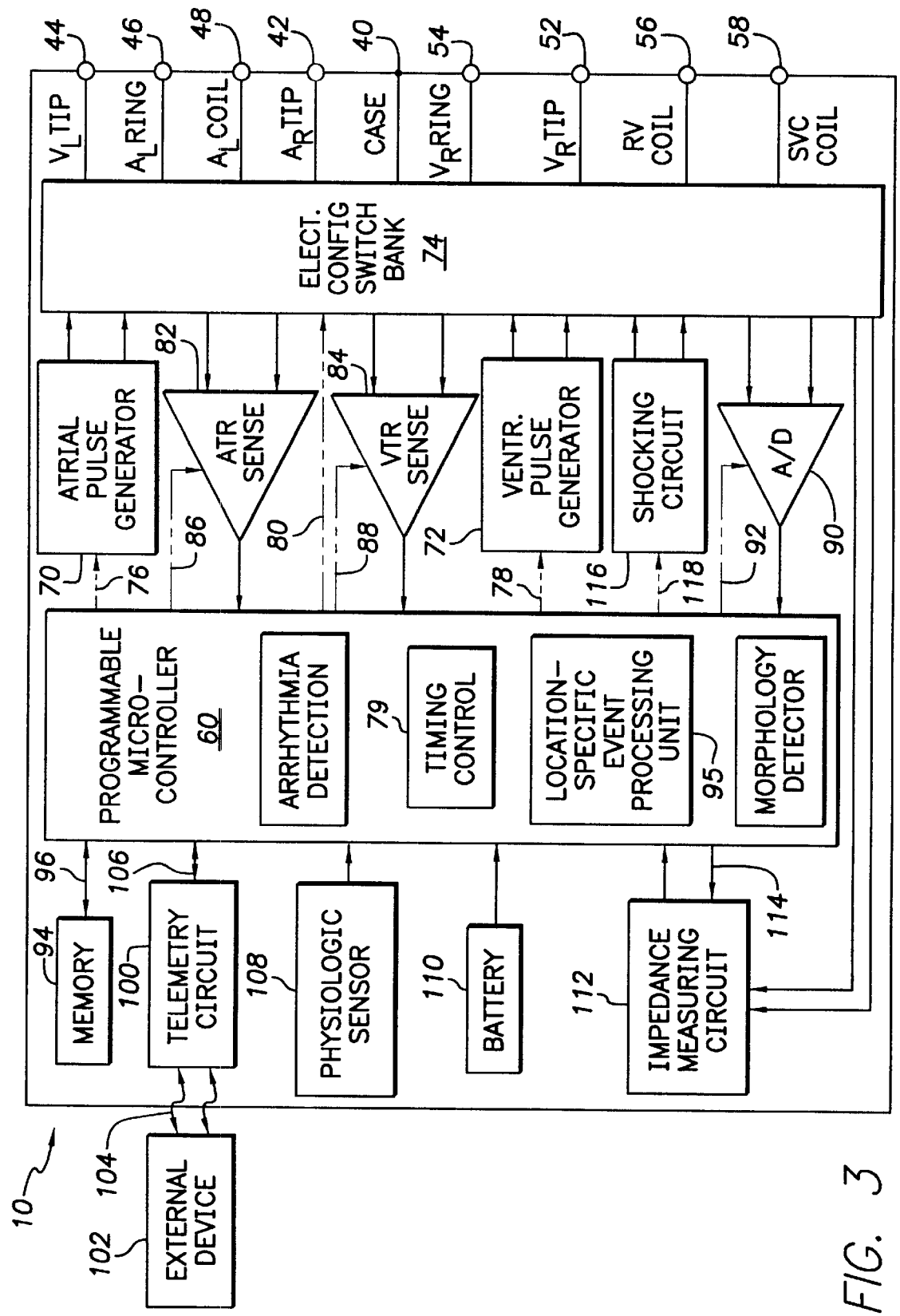
FIG. 3 is a functional block diagram of the implantable stimulation device of FIG. 2 illustrating the basic elements of the stimulation device and also illustrating, in block diagram form, an external programmer device for use with the stimulation device.
Figure 4:
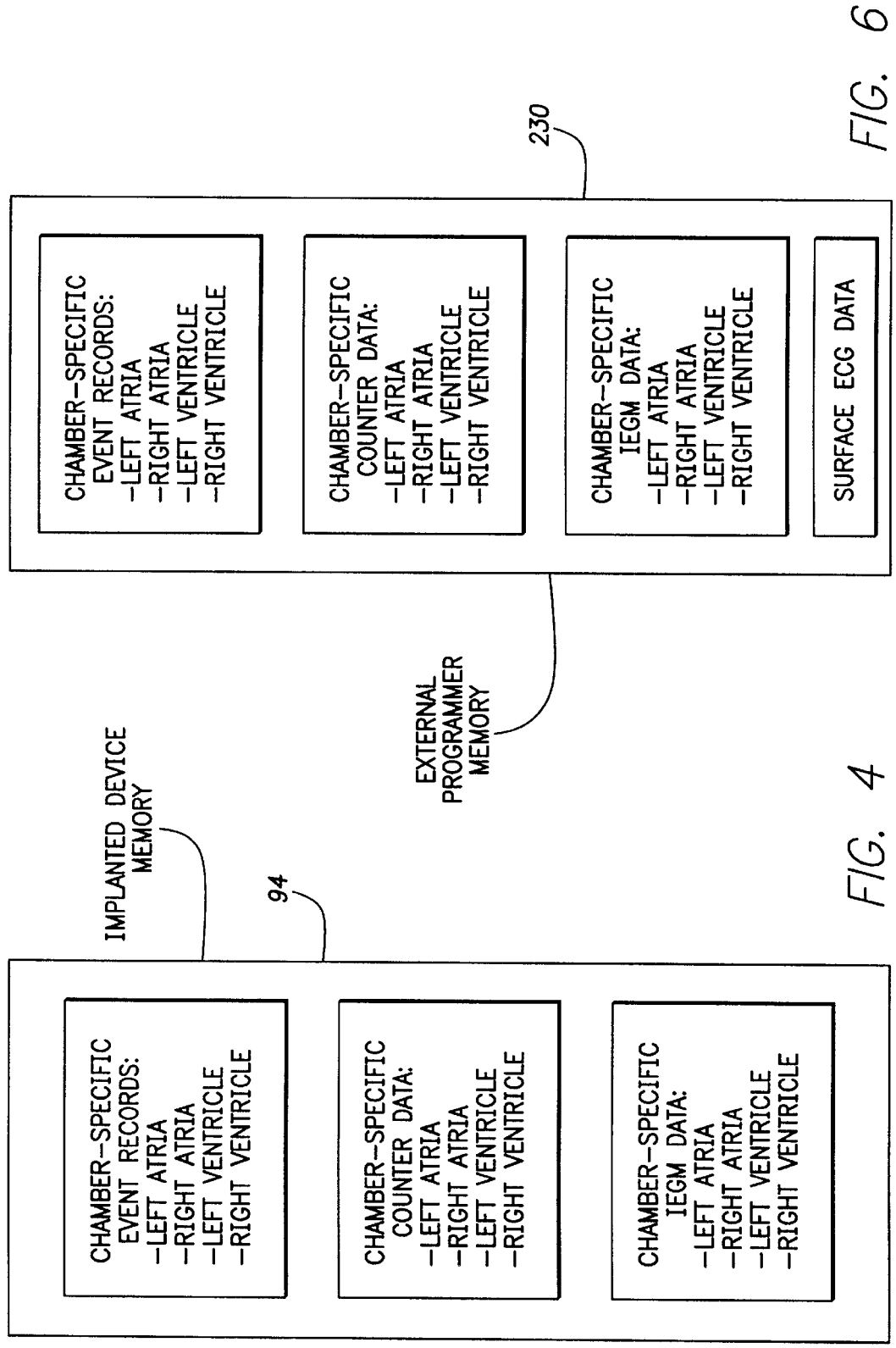
FIG. 4 is a block diagram illustrating a portion of a memory of the implantable device of FIGS. 2 and 3 for storing enhanced location-specific event codes, counters and IEGM signals.
Figure 5:
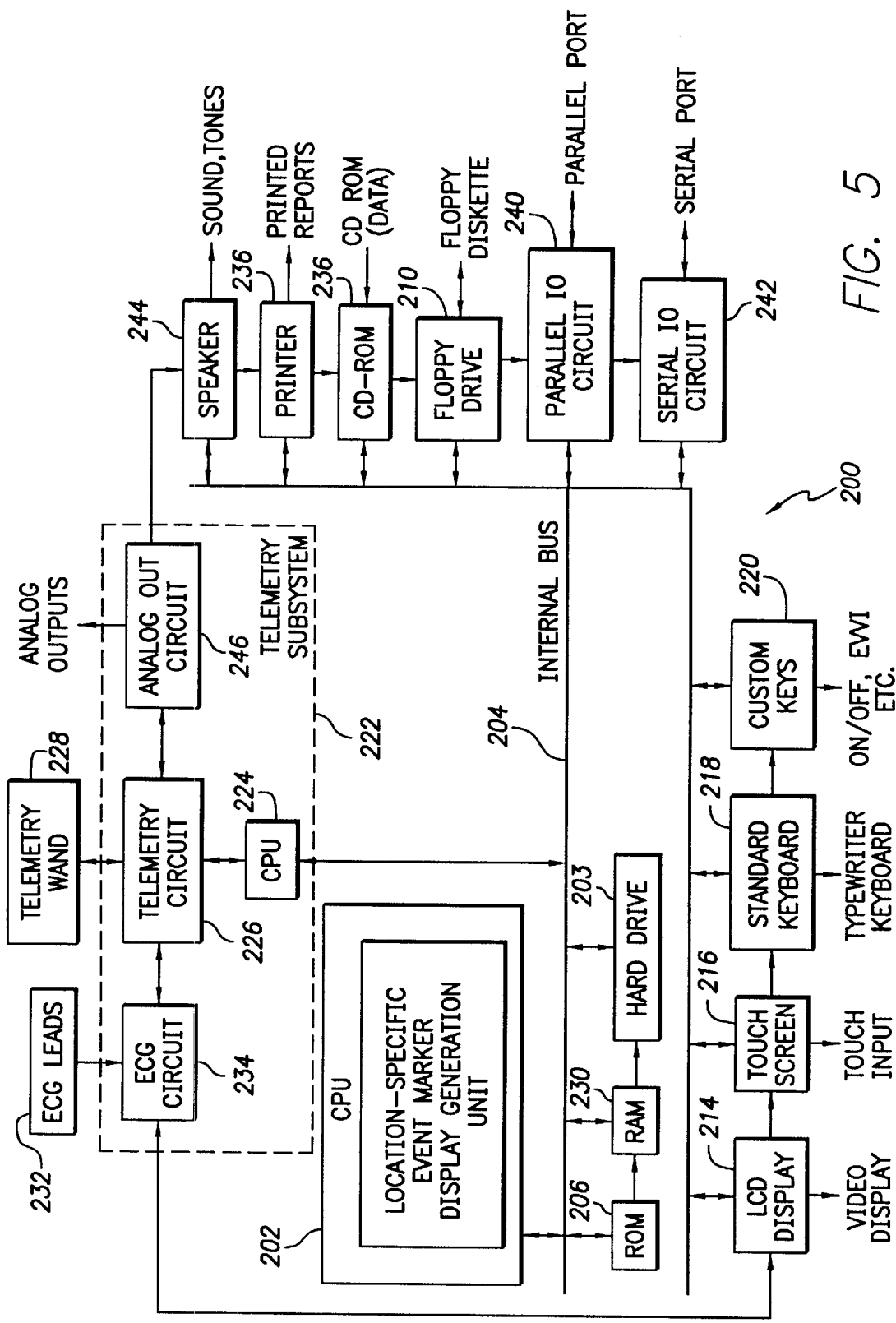
FIG. 5 is a block diagram of pertinent components of the external programmer of FIG. 3 for use in processing and displaying the event codes, counters and IEGM signals received from the device of FIGS. 1 and 2.

Herein, details of an exemplary implantable device are provided with reference to FIGS. 2–4, which illustrates a dual-chamber implantable stimulation device capable of provide cardioversion, defibrillation and pacing stimulation in four chambers of the heart. Then details regarding an exemplary external programmer are provided with reference to FIGS. 5 and 6. Thereafter, a method performed by the implantable device and the external programmer to generate and display the enhanced diagnostic information is described with reference to FIG. 7. Finally, various exemplary graphic displays generated by the external programmer are described with reference to the FIGS. 8–11B.

Stimulation Device

As shown in FIG. 2, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead" (Pianca et. al.); and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

As illustrated in FIG. 3, a simplified block diagram is shown of the multi-chamber implantable stimulation device 10, which is capable of treating both fast and slow rhythms with electrical therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 3, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

Thus, with the arrangement of leads of FIG. 2 and terminals of FIG. 3, the device is capable of separately sensing electrical signals in each of the four chambers of the heart. Additional leads and terminals may be provided to separately sense electrical signals at multiple locations within a particular chamber.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 3, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the invention is the ability to sense and store a relatively large amount of data (e.g., from the data acquisition system 90), which data may then be used for subsequent analysis to guide the programming of the device. In particular, the memory stores location-specific data such as location-specific event records and IEGM data. In a primary example described herein, the memory separately stores diagnostic data for each of the four chambers of the heart. A portion of memory 94 is shown in FIG. 4. As can be seen the memory stores location-specific event records, counter data and IEGM data for each of the four chambers of the heart. As will be described further below, the location-specific data is ultimately transmitted to an external programmer for display thereon. Processing of the location-specific data, including generation of the location-specific event records and the storage thereof in the memory, is controlled by a location-specific event processing unit 95 of the microcontroller. The location-specific event processing unit maybe a software module of a control program executed by the controller.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient Generation of Sensing Signals in an Implantable Medical Device such as a Pacemaker or ICD" (note: this relates to transfer of EGM data) (McClure et al.), which patents are hereby incorporated herein by reference.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 that provides operating power to all of the circuits shown in FIG. 3. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries or lithium iodine cells.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 3, the device 10 is shown as having an impedance measuring circuit 112 which is enabled by the microcontroller 60 via a control signal 114. The impedance measuring circuit 112 is not critical to the invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asychronously (since R-waves may be too disorganized), and pertaining exclusively to the treatment of fibrillation. Accordingly, the microcontroller 60 is capable of controlling the synchronous or asynchronous delivery of the shocking pulses.

External Programmer

FIG. 4 illustrates pertinent components of an external programmer for use in programming an implantable cardiac stimulation device such as the device of FIGS. 2 and 3. Briefly, the programmer permits a physician or other user to program the operation of the implanted device and to retrieve and display information received from the implanted device such as IEGM data and device diagnostic data. In particular, the programmer is provided with internal components capable of separately receiving, storing and processing event markers representative of events paced or sensed in any of the four chambers of the heart. Additionally, the external programmer receives and displays ECG data from separate external ECG leads that may be attached to the patient. Depending upon the specific programming of the external programmer, programmer 200 may also be capable of processing and analyzing data received from the implanted device and from the ECG leads to, for example, render preliminary diagnosis as to medical conditions of the patient or to the operations of the implanted device.

Now, considering the components of programmer 200, operations of the programmer are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206. Additional software may be accessed from a hard drive 208, floppy drive 210, and CD ROM drive 212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 214 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 216 overlaid on the LCD display or through a standard keyboard 218 supplemented by additional custom keys 220, such as an EVVI key.

Typically, the physician initially controls the programmer 200 to retrieve data stored within the implanted cardiac stimulation device and to also retrieve ECG data from ECG leads, if any, coupled to the patient. To this end, CPU 202 transmits appropriate signals to a telemetry subsystem 222, which provides components for directly interfacing with the implanted device, and the ECG leads. Telemetry subsystem 222 includes its own separate CPU 224 for coordinating the operations of the telemetry subsystem. Main CPU 202 of programmer communicates with telemetry subsystem CPU 224 via the internal bus. Telemetry subsystem additionally includes a telemetry circuit 226 connected to a telemetry wand 228, which, in turn, receives and transmits signals electromagnetically from a telemetry unit of the implanted device. The telemetry wand is placed over the chest of the patient in the vicinity of the implanted device to permit reliable transmission of data between the telemetry wand and the implanted device. Typically, at the beginning of the programming session, the external programming device controls the implanted device via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Preferably, all data stored within the implanted device is recorded within "event records" which facilitate the efficient storage and transmission of the data. Additional information pertaining to the recording, transmission, and processing of event record information may be found within the aforementioned U.S. patent to Snell. Unlike the system of Snell, however, the data provided by the stimulation device and the event markers displayed by the external programmer distinguish among a greater number of sensing locations, such as between the left and right chambers of the heart or among multiple locations within a single chamber of the heart. In the primary example described herein, the memory of the external programmer stores the location-specific event records, counter data and IEGM data for each of the four chambers of the heart received from the stimulation device. A portion of ROM 206 is shown in FIG. 6. As can be seen, the ROM stores location-specific event records, counter data and IEGM data for each of the four chambers of the heart. A location-specific event marker display generation unit within the CPU controls the generation of graphic displays of diagnostic information based on the location-specific event records, counter data and IEGM data stored in RM 206. The location-specific event processing unit maybe a software module of a control program executed by the CPU.

Data retrieved from the implanted device is stored by external programmer 200 either within a random access memory (RAM) 230, hard drive 208 or within a floppy diskette placed within floppy drive 210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted device is transferred to programmer 200, the implanted device may be further controlled to transmit additional data in real time as it is detected by the implanted device, such as additional IEGM data, lead impedance data, and the like. Additionally, or in the alternative, telemetry subsystem 222 receives ECG signals from ECG leads 232 via an ECG processing circuit 234. As with data retrieved from the implanted device itself, signals received from the ECG leads are stored within one or more of the storage devices of the external programmer. Typically, ECG leads output analog electrical signals representative of the ECG. Accordingly, ECG circuit 234 includes analog to digital conversion circuitry for converting the signals to digital data appropriate for further processing within programmer. Depending upon the implementation, the ECG circuit may be configured to convert the analog signals into event record data for ease of processing along with the event record data retrieved from the implanted device. Typically, signals received from the ECG leads are received and processed in real time.

Thus the programmer receives data both from the implanted device and from the external ECG leads. Data retrieved from the implanted device includes parameters representative of the current programming state of the implanted device. Under the control of the physician, the external programmer displays the current programming parameters and permits the physician to reprogram the parameters. To this end, the physician enters appropriate commands via any of the aforementioned input devices and, under control of CPU 202, the programming commands are converted to specific programming parameters for transmission to the implanted device via telemetry wand 228 to thereby reprogram the implanted device. Techniques for programming an implanted cardiac stimulation device may be found in U.S. Pat. No. 5,716,382 entitled "Programmer For An Implantable Cardiac Stimulating Device". Prior to reprogramming specific parameters, the physician may control the external programmer to display any or all of the data retrieved from the implanted device or from the ECG leads, including displays of ECGs, IEGMs, and statistical patient information. In particular, the external programmer can be controlled to generate graphic displays or printouts of location-specific IEGMs and event markers. Depending upon the programming of the external programmer and the commands entered, the programmer may display either a single combined IEGM representative of a combination of the IEGM signals from the four chambers of the heart or may display the individual IEGM signals separately. Further information pertaining to information that may be displayed using the programmer may be found in U.S. Pat. No. 5,974,341 entitled "Method And Apparatus For Detecting And Displaying Diagnostic Information In Conjunction With Intracardiac Electrograms And Surface Electrocardiograms". Any or all of the information displayed by programmer may also be printed using a printer 236.

Programmer 200 also includes a modem 238 to permit direct transmission of data to other programmers via the public switched telephone network (PSTN) or other interconnection line, such as a T1 line or fiber optic cable. Depending upon the implementation, the modem may be connected directly to internal bus 204 may be connected to the internal bus via either a serial port 240 or a parallel port 242. Other peripheral devices may be connected to the external programmer via serial port 240 or a parallel port 242 as well. Although one of each is shown, a plurality of input output (IO) ports may be provided. A speaker 244 is included for providing audible tones to the user, such as a warning beep in the event the physician provides improper input. Telemetry subsystem 222 additionally includes an analog output circuit 246 for controlling the transmission of analog output signals.

With the programmer configured as shown, a physician or other user operating the external programmer is capable of retrieving, processing and displaying a wide range of information received from the ECG leads or from the implanted device and to reprogram the implanted device if needed. The descriptions provided herein with respect to FIG. 4 are intended merely to provide an overview of the operation of programmer and are not intended to describe in detail each and every feature of the hardware and software of the device and is not intended to provide an exhaustive list of the functions performed by the device.

Processing of Location-Specific Diagnostic Data

Figure 7:
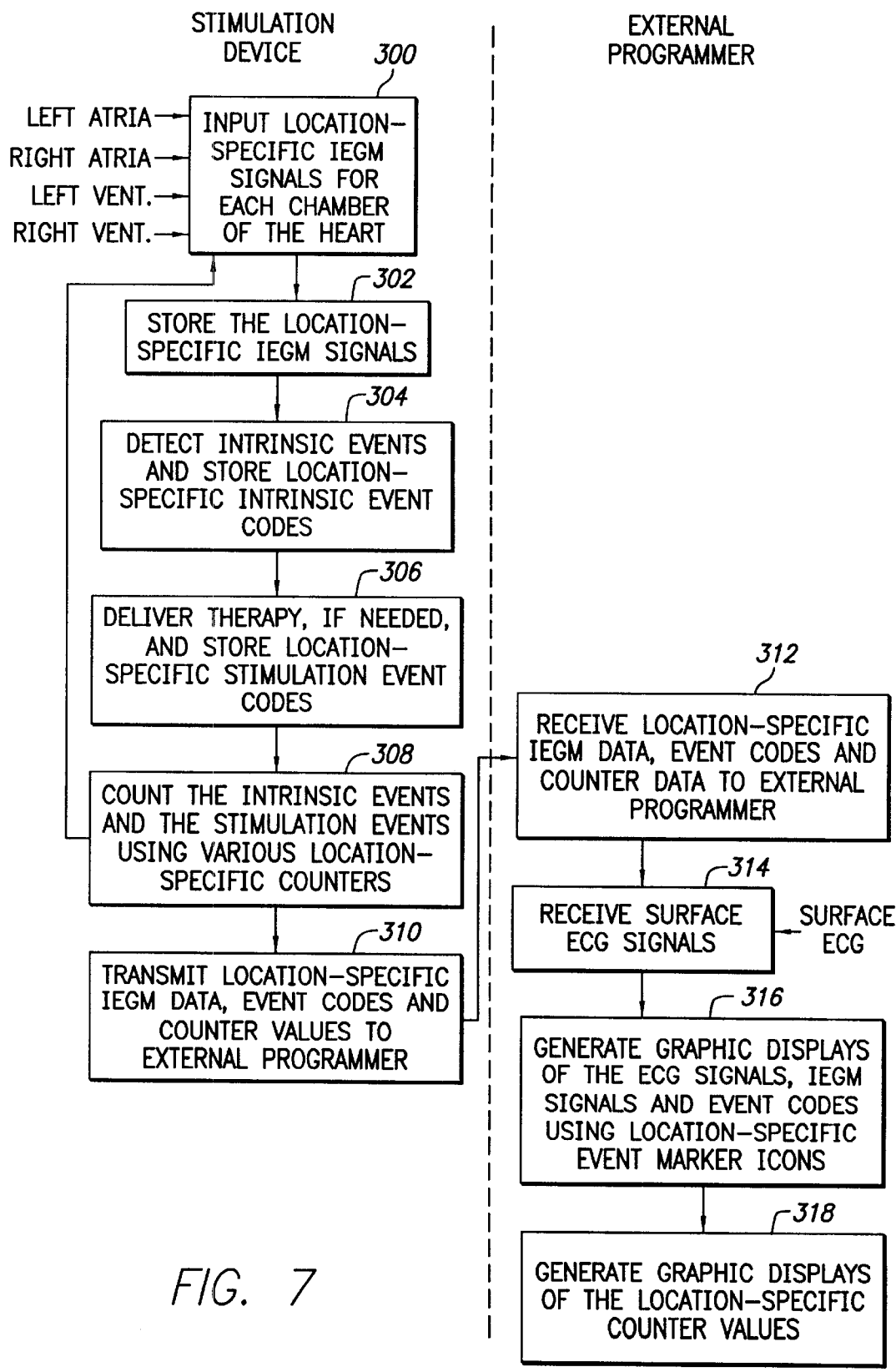
FIG. 7 is a flow chart illustrating a method performed by the system of FIGS. 2–6 for generating, processing, recording, and displaying enhanced location-specific diagnostic information that distinguishes among the chambers of the heart.

FIG. 7 is a flow chart illustrating the operation of the programmer and implantable device to permit the physician to generate printouts and displays of location-specific diagnostic data such as IEGMs and event markers. In the flow chart, the various steps of the method are summarized in individual "blocks". Such blocks describe specific actions or decisions that are made or carried out as the method proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein. Steps performed by the implanted device are shown on the left. Steps performed by the external programmer are shown on the right.

Briefly, the implanted device operates to record IEGM signals and to detect, record and count location-specific events while distinguishing among the various chambers of the heart. The stimulation device transmits the data to the external programmer, which operates to display event marker icons identifying the location-specific events along with the IEGM signals received from the stimulation device or along with separately detected surface ECG signals. The external programmer also operates to display the counts of the location-specific events in the form of histograms or other graphical displays.

Initially, at step 300, the implantable stimulation device inputs separate location-specific IEGM signals from each of the four chambers of the heart via the aforementioned sensing leads. Hence, at step 300, the stimulation device receives separate left and right atrial IEGM signals and separate left and right ventricular IEGM signals. At step 302 the location-specific IEGM signals are stored within an internal memory of the stimulation device (memory 94 of FIG. 3). As the signals are received, the stimulation device analyzes the location-specific IEGM signals to detect and record intrinsic deflection events found therein, at step 304. The intrinsic events detected within the right and left atria and right and left ventricles are internally designated and recorded using event codes identifying the specific chamber. Other sensed information may also be detected and recorded such as the lengths of refractory periods and the like. Each intrinsic event, as it is recorded, is also time stamped to indicate the date and time of the event. Depending upon the intrinsic events detected within the IEGM signals and on the programming of the implanted stimulation device, the stimulation device delivers therapy at step 306 usually in the form of individual pacing pulses delivered to one or more of the chambers of the heart. The stimulation device also records the stimulation events at step 306 in the memory along with the detected intrinsic events. Stimulation administered to the right and left atria and right and left ventricles is internally designated and recorded using event codes identifying the specific chamber. Stimulation administered to multiple chambers simultaneously is internally designated and recorded using a appropriate multi-chamber event codes. Depending upon its programming and capabilities, the stimulation device also may be capable of sensing in one chamber and delivering a responsive pacing pulse in another chamber. This is desirable if, for example, an intrinsic pacing event is detected in only the left ventricle rather than within both the left and right ventricles. If the stimulation device is capable of sensing in one chamber, then pacing in another, or vice versa, the two events are stored separately along with a code indicating that the two events are related. As will be described below, the programmer detects related events and generates a unique display. Each stimulation event, as it is recorded, is also time stamped to indicate the date and time of the event. Preferably, the intrinsic events and stimulation events are recorded using the event record format of the aforementioned Snell patent, modified as needed to accommodate the various location-specific event codes. The actual event codes may be any suitable alphanumerical codes or other codes suitable for distinguishing the events for storage within the memory. They may, for example, be unique sequences of binary numbers.

Also as events are recorded, various internal counters maintained by the stimulation device are updated, at step 308, to track the various events. For example, separate location-specific intrinsic event counters are incremented whenever an intrinsic event is detected within one or more of the separate IEGM signals. The counters may have separate bins or registers for different heart rate ranges to permit location-specific histograms of intrinsic events to be recorded as a function of heart rate. Other counters may be provided for separately tracking events that are not location-specific, such stimulation events occurring in both left and right chambers. For example, for stimulation pulses applied to both ventricles, a dual chamber ventricular stimulation counter is updated. In other cases, although events may be separately detected in different chambers, a single counter may be used to count the sum total of all events in the separate chambers. For example, a counter may be provided to count all intrinsic events in the atria, without distinguishing between the left and right atria. Other counters may be provided to tracking coupling intervals between successive complexes based on whether a premature beat or an intrinsic beat arises from the left or right atria or left or right ventricle. As can be appreciated, a wide variety of counters may be employed for tracking a wide variety of information. No attempt is made herein to enumerate or describe the many counters that may be employed. In general, any conventional non-location-specific counter can be modified, in accordance with the principles of the invention, to separately count location-specific data.

Steps 300–308 are continuously performed while the stimulation device is operating within the patient to process newly received location-specific IEGM signals from the various chambers of the heart and to store location-specific event records and to update location-specific counters. Preferably, sufficient internal memory is provided to store the location-specific IEGM signals and event records over a relatively long period of time to permit subsequent transmission to the external programmer. If the event record memory or the IEGM memory becomes full, the earliest recorded IEGM signals and event records are preferably overwritten by newly detected IEGM signals and event records.

Subsequently, perhaps during a follow-up session with the physician, the implantable stimulation device is controlled at step 310 to transmit the location-specific event records, IEGM data, and counter values and any other diagnostic information to the external programmer. The programmer may request that all previously recorded event records and IEGM data be transferred to the programmer or that only event records and IEGM data associated with specific periods of time be transmitted. Alternatively, the programmer may request that only real-time IEGM data and event records be transmitted such that the physician may generate displays of current conditions within the heart of the patient and within the implantable device.

The programmer at step 312 receives and stores the transmitted data. At step 314, the programmer receives surface ECG data, if available, and at step 316 generates corresponding graphic displays or printouts of the location-specific event records and IEGM data and the surface ECG signals. To this end, for each event recorded in the event record data, event markers are generated and displayed using icons that distinguish among the different types of events and among the four chambers of the heart. For example, L and R subscripts may be employed to distinguish between left and right chambers of the heart. A D subscript may be employed to represent a dual chamber event. In one specific example, the following icons are used to represent intrinsic events detected in the right and left atria and right and left ventricles respectively: $P_R$, $P_L$, $R_R$, and $R_L$. Also in the example, the following icons are used to represent stimulation events applied to the right and left atria and right and left ventricles respectively: $A_R$, $A_L$, $V_R$, and $V_L$. Dual chamber pacing in the atria is represented by $A_D$ whereas dual chamber pacing in the ventricles is represented by $V_D$.

As can be appreciated, numerous other representation systems may be employed. The various event markers and icons described above are merely exemplary. For example, rather than providing $R_L$ to identify an intrinsic event detected in the left ventricle, the system may employ a $V_{SL}$. Likewise, rather than using a $P_R$ to identify an intrinsic event sensed in the right atrium, the system may instead employ a $A_{SR}$ to identify the same event. If two or more pacing or sensing sites are located within a single chamber of the heart, numerical indices may be employed to distinguish there-between. For example, an intrinsic event detected at a first sensing location within the left atrium may be identified using the event marker $P_{L1}$ whereas an intrinsic event detected at a second location within the left atrium may be identified using the event marker $P_{L2}$. Depending upon the programming of the system, and the display capabilities of the programmer, different colors may be employed to distinguish different event marker icons.

Preferably, the event marker icons are displayed along side either the IEGM data, the ECG data or both. Any other data provided by the stimulation device is displayed numerically or graphically depending upon the nature of the data and the preferences of the physician. For example, refractory periods are displayed using horizontal bars. Insofar as the IEGM data is concerned, because the programmer receives four separate IEGM data streams corresponding to the four chambers of the heart, there is considerable flexibility as to the generation of IEGM graphic displays. Under the control of the physician, the programmer may display, for example, a single IEGM signal that represents a combination of the four separate IEGM channels. In this regard, appropriate filtering or averaging software may be employed to combine the four IEGM channels into a single IEGM signal. Alternatively, the physician may wish to display IEGM signals wherein left and right chambers are averaged together, but wherein separate displays are presented for the atrial and ventricular signals. In still other cases, the physician may wish to display all four individual IEGM signals. As can be appreciated, wide ranges of choices are available to the physician. In each case, event markers are preferably displayed alongside the IEGM signals to indicate the relative timing relationship of the events and the portions of the IEGM signals displayed.

Figure 1:
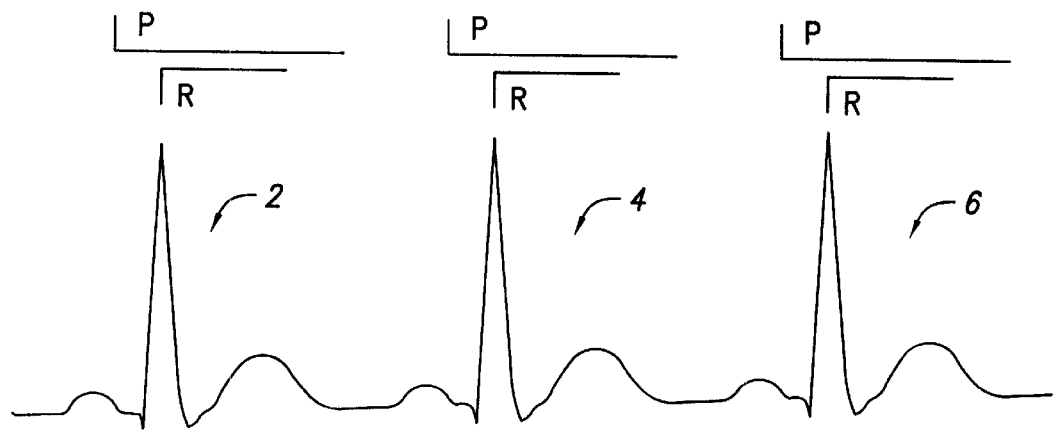
FIG. 1 is illustrates an exemplary display of surface ECG complexes and a set of conventional event markers displayed by an external programmer in accordance with the prior art.

FIG. 8 is an exemplary display of enhanced event markers in combination with the same ECG complexes of FIG. 1 (now denoted 332, 334 and 336). Unlike the conventional event markers of FIG. 1, the event markers of FIG. 8 properly show that the events of complexes 332 and 336 were detected within the right chambers of the heart and the events of complex 334 were detected within the left chambers. A short vertical tick mark is displayed precisely indicating the point in time the corresponding event was detected. FIG. 8 also illustrates the use of horizontal lines or bars to indicate the length of refractory periods associated with the P-waves and R-waves.

As noted above, the implanted device may be programmed to deliver a stimulation pulse to the right ventricle if an intrinsic pacing event is detected only in the left ventricle, or vice versa. If this is the case, the device thereby stores related event markers. Upon detecting a pair of related event markers, the programmer displays both event markers along with the ECG complex and employs two short vertical tick marks to indicate the related sensed/paced events. An example is illustrated in FIG. 9. As can be seen, two short vertical tick marks are displayed along with adjacent $R_R$ and $V_L$ event marker icons indicating that an intrinsic event was detected in the right ventricle and a stimulation pulse was generated in the left ventricle.

FIG. 10 illustrates a combination display of both atrial and ventricular IEGM signals and a surface ECG complex 337 along with location-specific event marker icons. The figure specifically illustrates an intrinsic atrial deflection point 338 used by the implanted device to detect the intrinsic atrial event and an intrinsic ventricular deflection point 340 used by the implanted device to detect the intrinsic ventricular event. In the example of FIG. 10, only a single atrial IEGM signal is illustrated and only a single ventricular IEGM signal is illustrated. In other embodiments, separate left and right atrial and left and right ventricular IEGM signals are displayed by the external programmer.

Figure 11A:
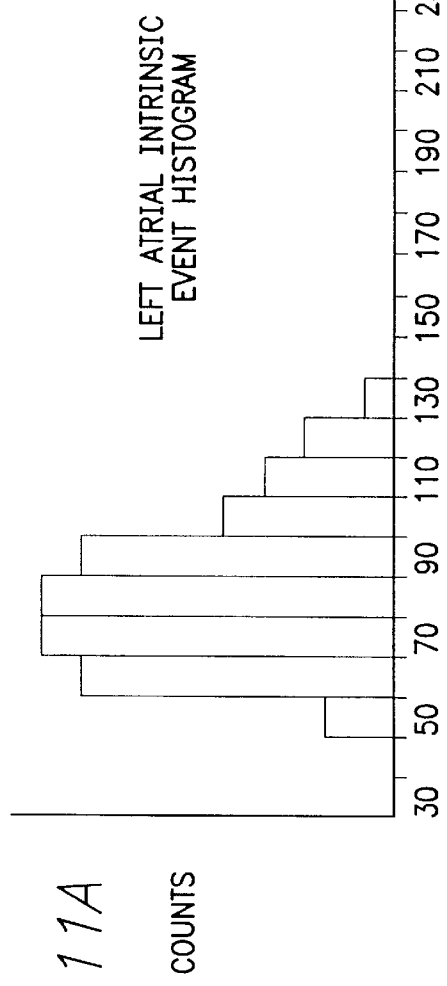
FIGS. 11A and 11B are graphs illustrating exemplary location-specific histograms as displayed by the external programmer of FIG. 5.
Figure 11B:
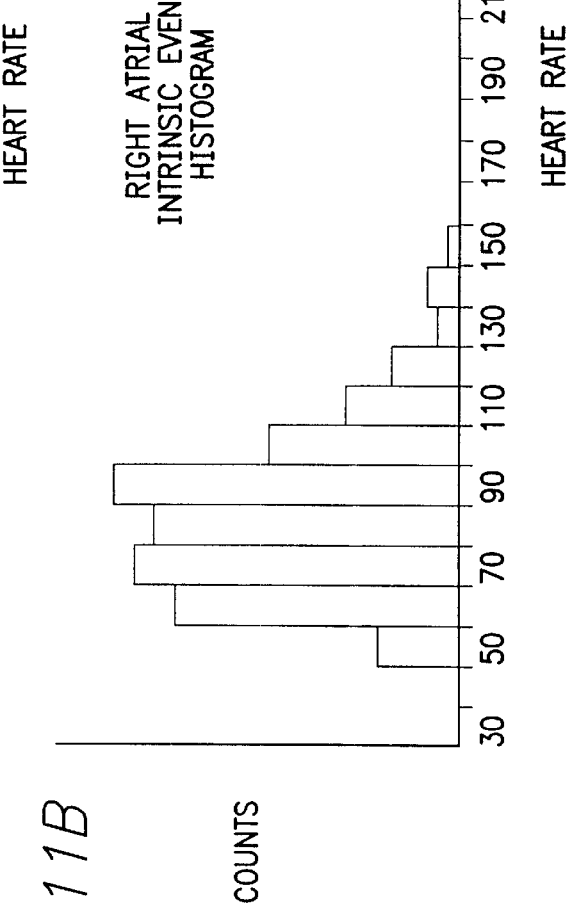

Returning again to the flow chart of FIG. 7, at step 318 the programmer generates graphic displays or printouts of the location-specific counter values such as location-specific histograms and the like. FIGS. 11A and 11B illustrates a pair of location-specific histograms illustrating counts of intrinsic events detected in the left and right atria as a function of heart rate. Other location-specific histograms may be displayed as well such as histograms illustrating counts of intrinsic events detected in the left and right ventricles as a function of heart rate or histograms illustrating counts of stimulation events in the various chambers of the heart.

What has been described are systems for generating, storing, processing and graphically displaying a wide variety of information pertaining to events detected by an implantable cardiac stimulation device. The various functional components of the exemplary system may be implemented using any appropriate technology including, for example, microprocessors running software programs or application specific integrated circuits (ASICs) executing hard-wired logic operations. Although described with respect to a pacemaker used in conjunction with an external programmer, aspects of the invention are applicable to other systems, such as systems employing other implantable cardiac stimulation devices or systems employing other types of external interfaces for use with the implantable device. The exemplary embodiments of the invention described herein are merely illustrative of the invention and should not be construed as limiting the scope of the invention.

What is claimed is:

1. In an external programmer for use with an implantable cardiac stimulation device, a system for processing diagnostic information received from the stimulation device comprising:

means for receiving location-specific event codes transmitted from the implantable cardiac stimulation device, with at least two distinct location-specific event codes being associated with the atria or with at least two distinct location-specific event codes being associated with the ventricles; and means for generating graphic displays of location-specific event marker icons representative of the event codes, with a distinct location-specific event marker icon associated with each distinct location-specific event code;

wherein the means for generating graphic displays of location-specific event marker icons generates icons that distinguish between the left and right atria.

2. The external programmer of claim 1:

wherein the means for receiving location-specific event codes also receives refractory period information associated with the event codes; and wherein the means for generating graphic displays also generates graphic displays of the refractory periods.

3. The external programmer of claim 1:

wherein the means for receiving location-specific event codes also receives information linking related event codes; and wherein the means for generating graphic displays also generates graphics indicative of the linking of related event codes.

4. The external programmer of claim 1:

wherein the means for receiving location-specific event codes also receives location-specific intracardiac electrograms (IEGMs); and wherein the means for generating graphic displays also generates graphic displays of the location-specific IEGMs.

5. The external programmer of claim 1, further including means for receiving surface electrocardiograms (ECGs) and wherein the means for generating graphic displays also generates graphic displays of the surface ECGs.

6. In an external programmer for use with an implantable cardiac stimulation device, a system for processing diagnostic information received from the stimulation device comprising:

means for receiving location-specific event codes transmitted from the implantable cardiac stimulation device, with at least two distinct location-specific event codes being associated with the atria or with at least two distinct location-specific event codes being associated with the ventricles; and means for generating graphic displays of location-specific event marker icons representative of the event codes, with a distinct location-specific event marker icon associated with each distinct location-specific event code;

wherein the means for generating graphic displays of location-specific event marker icons generates icons that distinguish between the left and right ventricles.

7. The external programmer of claim 6 wherein the means for generating graphic displays of location-specific event marker icons also generates icons representative of stimulation events occurring simultaneously in multiple chambers of the heart.

8. The external programmer of claim 6:

wherein the means for receiving location-specific event codes also receives refractory period information associated with the event codes; and wherein the means for generating graphic displays also generates graphic displays of the refractory periods.

9. The external programmer of claim 6:

wherein the means for receiving location-specific event codes also receives information linking related event codes; and wherein the means for generating graphic displays also generates graphics indicative of the linking of related event codes.

10. The external programmer of claim 6:

wherein the means for receiving location-specific event codes also receives location-specific intracardiac electrograms (IEGMs); and wherein the means for generating graphic displays also generates graphic displays of the location-specific IEGMs.

11. The external programmer of claim 6 further including means for receiving surface electrocardiograms (ECGs) and wherein the means for generating graphic displays also generates graphic displays of the surface ECGs.

12. The system of claim 6 wherein the stimulation device has a plurality of leads positioned at different locations within the heart of the patient with at least two leads positioned within the atria or with at least two leads positioned within the ventricles.

13. The system of claim 6 wherein the stimulation device further comprises:

means for receiving signals representative of electrical events detected at the respective locations of the leads;

means for generating a stimulation signals using selected leads;

means for generating location-specific event codes representative of events occurring at the respective locations of the leads, with at least two distinct location-specific event codes being associated the atria or with at least two distinct location-specific event codes being associated with the ventricles; and means for transmitting the location-specific event codes to the external programmer.

14. The system of claim 13 wherein at least two leads are positioned in the atria and wherein the means for generating location-specific event codes generates codes that distinguish between the left and right atria.

15. The system of claim 13 wherein at least two leads are positioned in the ventricles.

16. The system of claim 13 wherein at least one lead is positioned in each chamber of the heart and wherein the means for generating location-specific event codes generates codes that distinguish among the four chambers of the heart.

17. The system of claim 13 wherein the means for generating a stimulation signal generates dual chamber stimulation signals using at least two leads in separate chambers of the heart and wherein the means for generating event codes also generates event codes representative of the dual chamber stimulation signals.

18. In an external programmer for use with an implantable cardiac stimulation device, a system for processing diagnostic information received from the stimulation device comprising:

means for receiving location-specific event codes transmitted from the implantable cardiac stimulation device, with at least two distinct location-specific event codes being associated with the atria or with at least two distinct location-specific event codes being associated with the ventricles; and means for generating graphic displays of location-specific event marker icons representative of the event codes, with a distinct location-specific event marker icon associated with each distinct location-specific event code;

wherein the means for generating graphic displays of location-specific event marker icons generates icons that distinguish among the four chambers of the heart.

19. In an external programmer for use with an implantable cardiac stimulation device, a system for processing diagnostic information received from the stimulation device comprising:

means for receiving location-specific event codes transmitted from the implantable cardiac stimulation device, with at least two distinct location-specific event codes being associated with the atria or with at least two distinct location-specific event codes being associated with the ventricles; and means for generating graphic displays of location-specific event marker icons representative of the event codes, with a distinct location-specific event marker icon associated with each distinct location-specific event code;

wherein the means for receiving location-specific event codes also receives counts of location-specific events, with the counts distinguishing among events occurring at different locations within the heart; and wherein the means for generating graphic displays also generates graphic displays of the counts of the events.

20. The external programmer of claim 19, wherein the means for receiving location-specific event codes also receives the counts as a function of heart rate; and wherein the means for generating graphic displays generates histograms of the counts as a function of heart rate.

21. In an external programmer for use with an implantable cardiac stimulation device, a system for processing diagnostic information received from the stimulation device comprising:

a telemetry system operative to receive location-specific event codes transmitted from the implantable cardiac stimulation device, with at least two distinct location-specific event codes being associated with the atria or with at least two distinct location-specific event codes being associated with the ventricles; and a location-specific event processing unit operative to generate graphic displays of location-specific event marker icons representative of the event codes, with a distinct location-specific event marker icon associated with each distinct location-specific event code;

wherein the location-specific event processing unit generates icons that distinguish between the left and right atria.

22. The external programmer of claim 21:

wherein the telemetry system also receives refractory period information associated with the event codes; and wherein the location-specific event processing unit also generates graphic displays of the refractory periods.

23. The external programmer of claim 21:

wherein the telemetry system also receives information linking related event codes; and wherein the location-specific event processing unit also generates graphics indicative of the linking of related event codes.

24. The external programmer of claim 21:

wherein the telemetry system also receives location-specific intracardiac wherein the location-specific event processing unit also generates graphic displays of the location-specific IEGMs.

25. The external programmer of claim 21 further including an ECG input system operative to receive surface electrocardiograms (ECGs) and wherein the location-specific event processing unit also generates graphic displays of the surface ECGs.

26. In an external programmer for use with an implantable cardiac stimulation device, a system for processing diagnostic information received from the stimulation device comprising:

a telemetry system operative to receive location-specific event codes transmitted from the implantable cardiac stimulation device, with at least two distinct location-specific event codes being associated with the atria or with at least two distinct location-specific event codes being associated with the ventricles; and a location-specific event processing unit operative to generate graphic displays of location-specific event marker icons representative of the event codes, with a distinct location-specific event marker icon associated with each distinct location-specific even code;

wherein the location-specific event processing unit generates icons that distinguish between the left and right ventricles.

27. The external programmer of claim 26 wherein the location-specific event processing unit also generates icons representative of stimulation events occurring simultaneously in multiple chambers of the heart.

28. The external programmer of claim 26:

wherein the telemetry system also receives counts of locations-specific events, with the counts distinguishing among events occurring at different locations within the heart; and wherein the location-specific event processing unit also generates graphic displays of the counts of the events.

29. The external programmer of claim 28:

wherein the telemetry system receives the counts as a function of heart rate; and wherein the location-specific event processing unit generates histograms of the counts as a function of heart rate.

30. The external programmer of claim 26:

wherein the telemetry system also receives refractory period information associated with the event codes; and wherein the location-specific event processing unit also generates graphic displays of the refractory periods.

31. The external programmer of claim 26:

wherein the telemetry system also receives information linking related event codes; and wherein the location-specific event processing unit also generates graphics indicative of the linking of related event codes.

32. The external programmer of claim 26:
wherein the telemetry system also receives location-specific intracardiac electrograms (IEGMs); and
wherein the location-specific event processing unit also generates graphic displays of the location-specific IEGMs.

33. The external programmer of claim 26 further including an ECG input system operative to receive surface electrocardiograms (ECGs) and wherein the location-specific event processing unit also generates graphic displays of the surface ECGs.

34. The system of claim 26 wherein the stimulation device has a plurality of leads positioned at different locations within the heart of the patient with at least two leads positioned within the atria or with at least two leads positioned within the ventricles.

35. In an external programmer for use with an implantable cardiac stimulation device, a system for processing diagnostic information received from the stimulation device comprising:
a telemetry system operative to receive location-specific event codes transmitted from the implantable cardiac stimulation device, with at least two distinct location-specific event codes being associated with the atria or with at least two distinct location-specific event codes being associated with the ventricles; and
a location-specific event processing unit operative to generate graphic displays of location-specific event marker icons representative of the event codes, with a distinct location-specific event marker icon associated with each distinct location-specific event code;
wherein the location-specific event processing unit generates icons that distinguish among the four chambers of the heart.

36. In an external programmer for use with an implantable cardiac stimulation device, a system for processing diagnostic information received from the stimulation device comprising:
means for receiving location-specific event codes transmitted from the implantable cardiac stimulation device, with at least one distinct location-specific event code associated with each of the four chambers of the heart;
means for receiving location-specific intracardiac electrograms (IEGMs) transmitted from the implantable cardiac stimulation device;
means for receiving surface electrocardiograms (ECGs);
means for generating graphic displays of location-specific event marker icons representative of the event codes, with a distinct location-specific event marker icon associated with each distinct location-specific event code; and
means for generating displays of the IEGMs and ECGs.

37. In an external programmer for use with an implantable cardiac stimulation device, a system for processing diagnostic information received from the stimulation device comprising:
a telemetry system operative to receive location-specific event codes transmitted from the implantable cardiac stimulation device, with at least one distinct location-specific event code associated with each of the four chambers of the heart;
the telemetry system also receiving location-specific intracardiac electrograms (IEGMs) transmitted from the implantable cardiac stimulation device and counts of location-specific event codes as a function of heart rate;
a surface electrocardiogram (ECG) input unit operative to input a surface ECG; and
a location-specific event processing unit operative to generate graphic displays of location-specific event marker icons representative of the event codes, with a distinct location-specific event marker icon associated with each distinct location-specific event code; with
the location-specific event processing unit also operative to generate graphic displays of the IEGMs and ECGs and graphic histogram displays of the counts of the event codes as a function of heart rate.

38. In an external programmer for use with an implantable cardiac stimulation device, a system for processing diagnostic information received from the stimulation device comprising:
means for receiving location-specific event codes transmitted from the implantable cardiac stimulation device, with at least one distinct location-specific event code associated with each of the four chambers of the heart;
means for receiving location-specific intracardiac electrograms (IEGMs) transmitted from the implantable cardiac stimulation device;
means for generating graphic displays of location-specific event marker icons representative of the event codes, with a distinct location-specific event marker icon associated with each distinct location-specific event code; and
means for generating displays of the IEGMs.

39. In an external programmer for use with an implantable cardiac stimulation device, a system for processing diagnostic information received from the stimulation device comprising:
a telemetry system operative to receive location-specific event codes transmitted from the implantable cardiac stimulation device, with at least one distinct location-specific event code associated with each of the four chambers of the heart;
the telemetry system also receiving location-specific intracardiac electrograms (IEGMs) transmitted from the implantable cardiac stimulation device and counts of location-specific event codes as a function of heart rate; and
a location-specific event processing unit operative to generate graphic displays of location-specific event marker icons representative of the event codes, with a distinct location-specific event marker icon associated with each distinct location-specific event code; with
the location-specific event processing unit also operative to generate graphic displays of the IEGMs and graphic histogram displays of the counts of the event codes as a function of heart rate.

* * * * *